US00PP24936P2

(12) United States Plant Patent
Tristram

(10) Patent No.: US PP24,936 P2
(45) Date of Patent: Sep. 30, 2014

(54) ***HIBISCUS* PLANT NAMED 'WALHIROSMO'**

(50) Latin Name: *Hibiscus syriacus×paramutabilis*
Varietal Denomination: WALHIROSMO

(76) Inventor: David Tristram, Arundel (GB)

( * ) Notice: Subject to any disclaimer, the term of this patent is extended or adjusted under 35 U.S.C. 154(b) by 167 days.

(21) Appl. No.: 13/507,780

(22) Filed: Jul. 25, 2012

Related U.S. Application Data

(60) Provisional application No. 61/574,217, filed on Aug. 1, 2011.

(51) Int. Cl.
*A01H 5/00* (2006.01)

(52) U.S. Cl.
USPC ..... Plt./257

(58) Field of Classification Search
CPC ..... A01H 5/02
USPC ..... Plt./257
See application file for complete search history.

*Primary Examiner* — June Hwu

(57) ABSTRACT

A new cultivar of *Hibiscus* named 'WALHIROSMO' that is characterized by robust upright open growth habit, glossy dark green foliage, and large sterile flat rose-pink flowers with contrasting red centers. In combination these traits set 'WALHIROSMO' apart from all other existing varieties of *Hibiscus* known to the inventor.

2 Drawing Sheets

Genus: *Hibiscus*.
Species: *syriacus×paramutabilis*.
Denomination: 'WALHIROSMO'.

BACKGROUND OF THE INVENTION

The present invention relates to a new and distinct cultivar of *Hibiscus*, which is grown as an ornamental shrub for use in the garden and landscape. The new cultivar is known botanically as *Hibiscus syriacus×paramutabilis*, and will be referred to hereinafter by the cultivar name 'WALHIROSMO'.

The inventor made his initial species cross between *Hibiscus syriacus* as female parent and *Hibiscus paramutabilis* as male parent in 1985, from which cross three of the most promising seedlings were retained to commence a long-term breeding aimed at achieving valuable commercial and aesthetic benefits, notably flower size, presentation and coloration. The breeding program is carried out at the inventor's nursery in Arundel, West Sussex, United Kingdom. Each new breeding cycle occupied from two to three years and required the production of each generation of new seedlings through the winter months, under lights. 'WALHIROSMO' was selected in 2002 from a cross made in 2000 between two unnamed and unreleased seedlings, both arising from the initial species cross. The parents of 'WALHIROSMO' were discarded without close description because the perceived benefits of 'WALHIROSMO' exceeded either of the parents. In particular, 'WALHIROSMO' exhibited larger and flatter flowers than either of the parents. The inventor selected 'WALHIROSMO' for its large well presented flat flowers which are rose-pink in color with a contrasting red center.

The closest comparison variety known to the inventor is *Hibiscus syriacus* 'Pink Giant' (unpatented) which also bears pink flowers with red eyes. Whereas the flowers of 'Pink Giant' may be described as saucer-shaped, and are 10 cm-12 cm in diameter, the flowers of 'WALHIROSMO' are flat or almost flat and are 17 cm-19 cm in diameter.

'WALHIROSMO' was first asexually propagated by the inventor in 2002 in Arundel, West Sussex, United Kingdom.

Asexual propagation was accomplished using semi-hardwood cuttings. Since that time, under careful observation, the distinguishing characteristics of 'WALHIROSMO' have been determined stable and uniform, and to reproduce true to type in successive generations of asexual propagation.

SUMMARY OF THE INVENTION

The distinguishing characteristics of 'WALHIROSMO' are as follows: In combination these traits set 'WALHIROSMO' apart from all other existing varieties of *Hibiscus* known to the inventor. 'WALHIROSMO' has not been tested under all possible conditions and phenotypic differences may be observed with variations in environmental, climatic, and cultural conditions.

1. Plants of 'WALHIROSMO' exhibit a healthy robust upright open growth habit.
2. The foliage of 'WALHIROSMO' is glossy dark green in color.
3. 'WALHIROSMO' bears rose pink flowers with contrasting red centers.
4. The flowers of 'WALHIROSMO' are large well presented flat blooms 17 cm-19 cm in diameter.
5. The flowers of 'WALHIROSMO' are sterile
6. At maturity, plants of 'WALHIROSMO' are 3 m in height and 1.8 m in width.
7. 'WALHIROSMO' prefers full sun in moist well drained growing media.
8. 'WALHIROSMO' is suitable for use as a garden specimen, mass plantings in the landscape, hedging and as container specimen.
9. 'WALHIROSMO' is hardy to at least in USDA Zone 5b.

DESCRIPTION OF THE DRAWINGS

The accompanying color drawings illustrate the overall appearance of 'WALHIROSMO' showing the colors of its foliage and flowers as true as it is reasonably possible to obtain in colored reproductions of this type.

The drawing labeled

The drawing labeled

Figure 1:
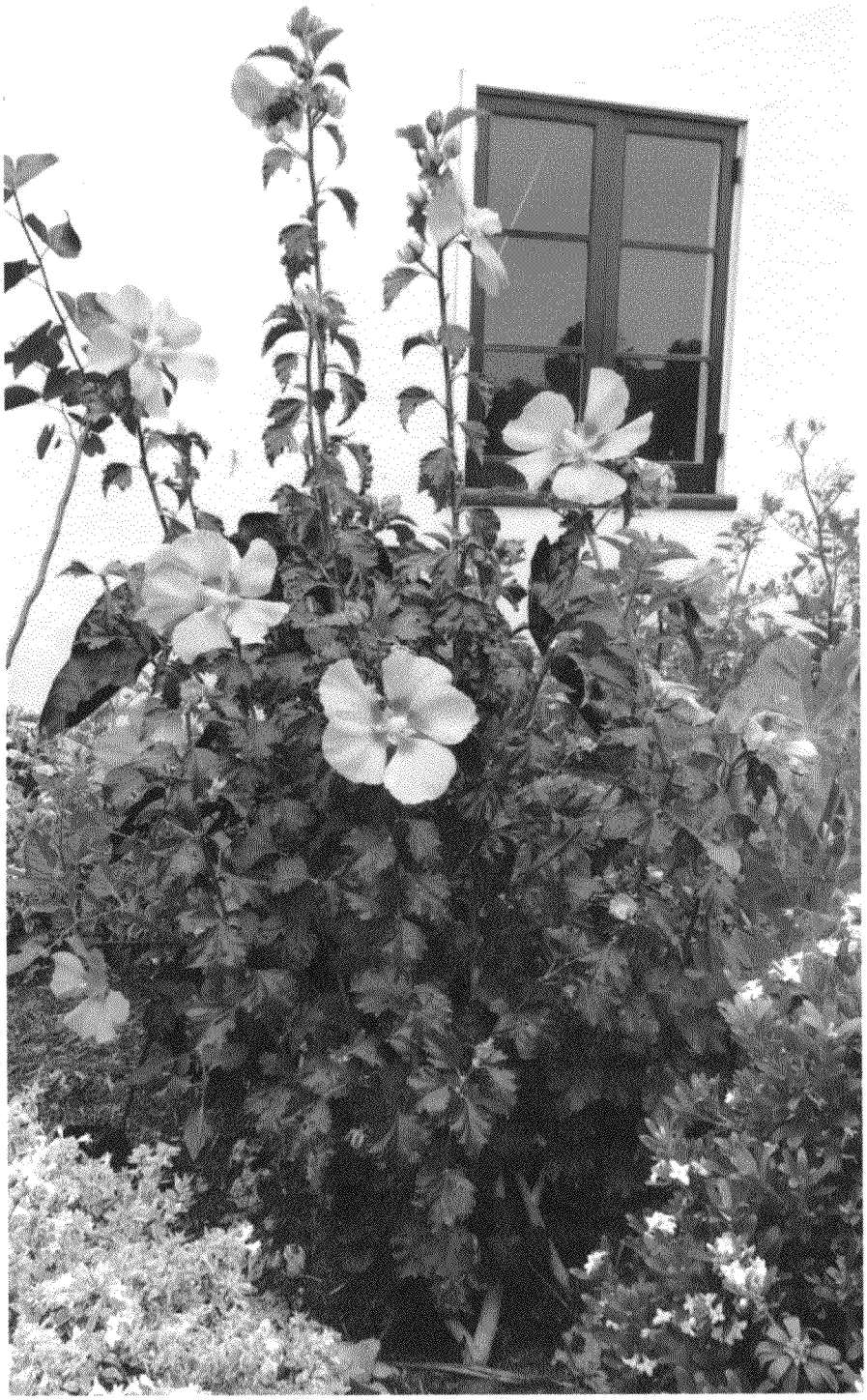
FIG. 1 shows a two year old plant of 'WALHIROSMO' which has been grown out of doors in the ground in Santa Barbara, Calif.
Figure 2:
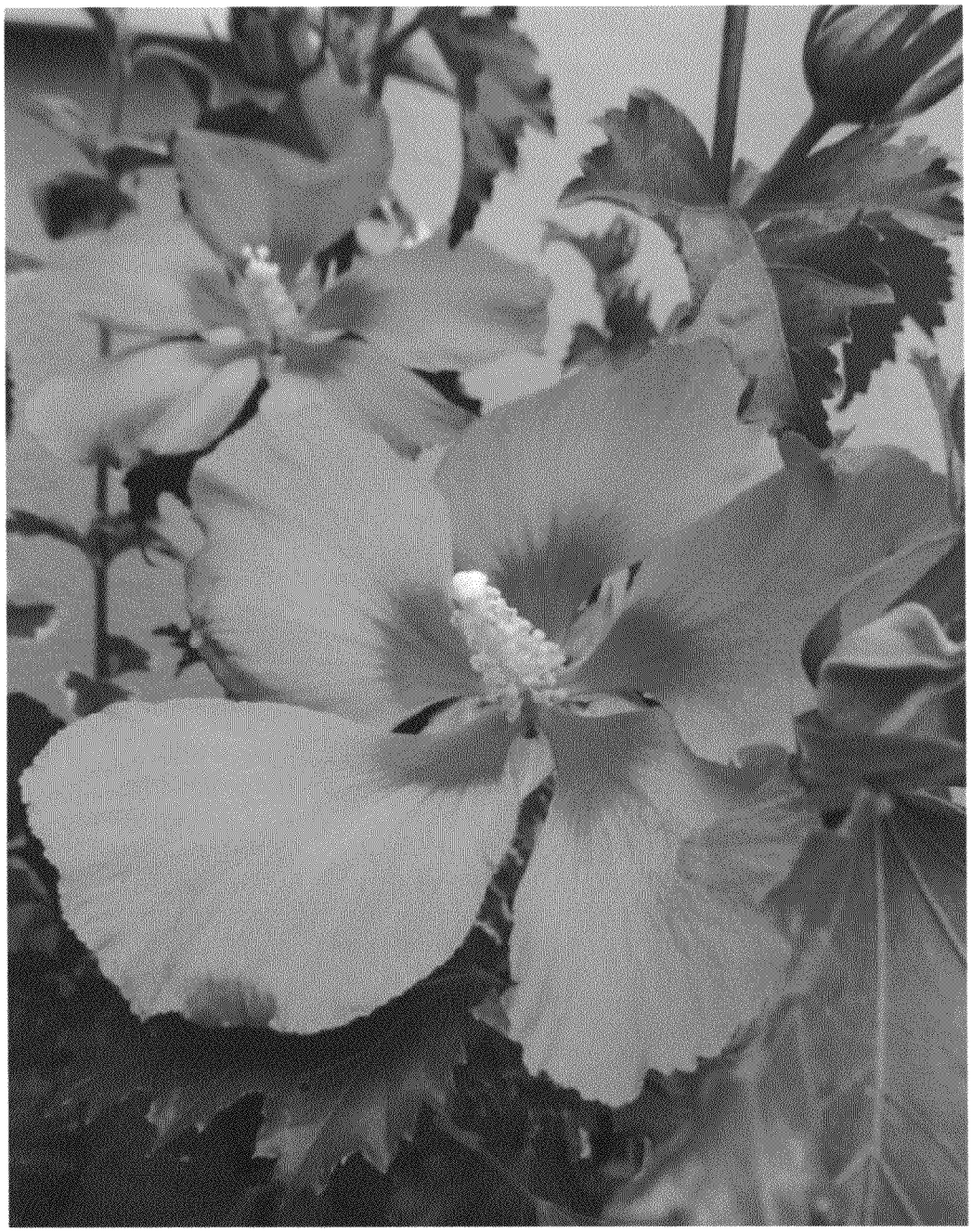
FIG. 2 depicts a close-up view of the flower of 'WALHIROSMO'.

The drawings were made using conventional techniques and although foliage and flower color may appear different from actual color due to light reflectance, they are as accurate as possible by conventional photography.

BOTANICAL DESCRIPTION OF THE PLANT

The following is a detailed description of the new *Hibiscus* cultivar named 'WALHIROSMO'. Data was collected during 2012 from two year old plants growing out-of-doors in Santa Barbara, Calif. Color determinations are in accordance with the fifth edition (2007) of The Royal Horticultural Society Colour Chart except where general color terms of ordinary dictionary significance are used.

Botanical classification: *Hibiscus syriacus×paramutabilis* 'WALHIROSMO'.
- *Genus.*—*Hibiscus.*
- *Species.*—*syriacus×paramutabilis.*
- *Denomination.*—'WALHIROSMO'.
- *Family.*—Malvaceae.
- *Common name.*—Rose of Sharon.

Uses: Ornamental landscape shrub or small tree, container plant and specimen plant.

Parentage: Unnamed and unreleased seedlings from the inventor's breeding program which commenced with the species cross between *Hibiscus syriacus* and *Hibiscus paramutabilis.*

Vigor: Vigorous.

Growth habit (unpinched): Upright, spreading slightly with age.

Plant dimensions in first year: 0.6 meter in height and 0.3 meter in width.

Plant dimensions in second year: 1.75 meter in height and 1 meter in width.

Hardiness: USDA Zone 5b.

Propagation: Soft or hardwood cuttings.

Root system: Fine and fibrous.

Cultural requirements: Full sun and humus-rich, fertile, well-draining soil, giving regular water during periods of growth.

Pest susceptibility: Susceptible to aphids and whitefly.

Disease susceptibility: None known to the inventor.

Time to initiate rooting (average): 21-28 days in a greenhouse with bottom heat to produce roots on semi-ripe cuttings.

Crop time: Requires 24 months from a cutting to produce a three-gallon container plant.

Special considerations: Prefers heat, tolerates some drought. Protect roots of young plants with mulch and prune plants to shape.

Plant:
- *Height.*—1.75 meters.
- *Diameter.*—1.0 meter.
- *Branching habit.*—Compact, upright, outwardly spreading in maturity.
- *Lateral branch quantity* (*range*).—7-12.

Trunk (main stem):
- *Trunk dimensions.*—1.0 m in height; 3cm in diameter at base, 0.5 cm in diameter at 1.0 m above the base.
- *Trunk shape.*—Cylindrical.
- *Trunk surface.*—Scurfy.
- *Trunk color* (*lower* 75 *cm*).—198D.
- *Trunk color* (*from* 75 *cm to* 1.0 *m*).—175A.

Stems (lateral branches):
- *Stem length.*—45-60 cm.
- *Stem diameter.*—4 mm-8 mm.
- *Stem color.*—Ranges from and between 137B when juvenile to 175A when mature and woody.
- *Stem texture.*—Smooth, glabrous.
- *Stem strength.*—Strong.
- *Stem surface.*—Glabrous.
- *Internode length* (*range*).—3 cm-10 cm.
- *Stem shape.*—Cylindrical.

Foliage:
- *Type.*—Deciduous.
- *Leaf arrangement.*—Spirally arranged.
- *Leaf quantity* (*average*).—15 per lateral stem.
- *Leaf length.*—8-10 cm.
- *Leaf width.*—6-7 cm.
- *Leaf color* (*adaxial surface*).—N137D.
- *Leaf color* (*abaxial surface*).—N138A.
- *Leaf division.*—Simple.
- *Leaf shape.*—Deltoid, three-lobed.
- *Leaf margin.*—Serrate. Teeth 3 mm in depth and spaced 3 per 1 cm.
- *Leaf base.*—Cuneate.
- *Leaf apex.*—Acute.
- *Leaf venation.*—Palmate.
- *Vein color* (*adaxial surface*).—139D.
- *Vein color* (*abaxial surface*).—138D.
- *Leaf surface* (*both surfaces*).—Smooth, glabrous.
- *Leaf attachment.*—Petiolate.
- *Leaf angle.*—Petiole held at 60°-90° away from the vertical.
- *Petiole dimensions.*—4 cm in length and 1.5 mm in diameter.
- *Petiole color.*—138A.
- *Petiole surface.*—Lightly flocculent.
- *Stipules.*—Present.
- *Stipule shape.*—Deltoid.
- *Stipule color* (*both surfaces*).—N137D.
- *Stipule surfaces* (*both*).—Smooth, glabrous.
- *Stipule dimensions.*—Various. From 1 cm-5 cm in length, 0.7-3 cm in width.
- *Foliar fragrance.*—None observed to date.

Inflorescence:
- *Inflorescence type.*—Single flowers, terminal and axillary.
- *Flower shape.*—Rotate.
- *Flower sexuality.*—Sterile.
- *Flower quantity* (*average*).—1 flower open and 6-10 buds per lateral branch.
- *Flower dimensions.*—5c m in depth and 17-19 cm in diameter.
- *Aspect.*—Facing outward. Peduncle held at 45° from the vertical.
- *Natural flowering season.*—July and August.
- *Persistent or self-cleaning.*—Self-cleaning.
- *Lastingness of flower.*—1-2 days on the plant.
- *Fragrance.*—None observed to date.

Petals:
- *Petal number.*—5.
- *Petal color* (*adaxial surface*).—From base extending 2.5 cm-3.5 cm: 61B. Remainder: N78B, except striations of 61B.

*Petal color* (*abaxial surface*).—From base extending 1 cm: 61C. Between 1 cm and 2.5 cm from base: 155A. Remainder: N78B.
*Petal veins* (*adaxial surface*).—Absent.
*Petal veins* (*abaxial surface*).—Present, prominent, palmate, appear as ribs extending from base to margin. Veins raised 1 mm, width up to 1 mm, color 155A becoming N78B.
*Petal length* (*average*).—9 cm in length.
*Petal width* (*average*).—8.5 cm in width.
*Petal margin*.—Medium serration and undulation.
*Petal shape* (*range*).—Orbicular to obovate.
*Petal arrangement*.—Petals touching to overlapping.
*Unfused or fused*.—Petals are unfused in relationship to one another but individually adnate to the stamen column.
*Petal surface* (*abaxial and adaxial surfaces*).—Glabrous, shiny.

Buds (about to open, color cracking):
*Bud color*.—138B.
*Bud apex* (*range*).—Obtuse.
*Bud base*.—Rounded.
*Bud shape*.—Urceolate.
*Bud dimensions*.—2.5 cm in height and 2.0 cm in diameter.
*Bud surface*.—Pubescent, scabrous.

Epicalyx (subtends calyx):
*Lobes*.—7, lanceolate, fused at base.
*Lobe dimensions*.—30 mm in length, 4-6 mm in width at base.
*Lobe color* (*both surfaces*).—137C.
*Lobe surface* (*both surfaces*).—Minutely scabrous.

Calyx, sepals:
*Calyx shape*.—Campanulate with 6 deltoid sepals fused at base.
*Calyx dimensions*.—1 cm in height, 4 cm in diameter.
*Calyx and sepal surface* (*both surfaces*).—Minutely scabrous.
*Sepal color* (*adaxial surface*).—138B.
*Sepal color* (*abaxial surface*).—144C.
*Sepal dimensions*.—18-20 mm in length, 7-10 mm in width at base.
*Sepal base*.—Truncate.
*Sepal apex*.—Acute.

Peduncle:
*Dimensions*.—4 cm in length and 3 mm-5 mm in width.
*Color of peduncle*.—144B.
*Surface of peduncle*.—Setose.

Reproductive organs:
*Stamens*.—Number: Between 100 and 200; filaments united into tube which clasps the style.
*Stamen color*.—NN155D.
*Anthers*.—Globular, 1-2 mm in diameter.
*Anther color*.—159A.
*Pollen*.—Moderate, grains approximately 0.5 mm in diameter.
*Pollen color*.—11C.
*Style*.—1, length 4 cm, diameter 8mm at base, 3 mm where pistil divides.
*Style color*.—Between pure white and slightly cream-white, closest to NN155C.
*Stigma*.—5, held on short white filaments.
*Stigma shape*.—Club-like, 3 mm long, 2 mm wide.
*Stigma color*.—NN155A.
*Ovary*.—Superior, globular, five-chambered.
*Ovary color*.—NN155A.
*Fruit and seed*.—None, 'WALHIROSMO' is sterile.

The invention claimed is:

1. A new and distinct variety of *Hibiscus* plant named 'WALHIROSMO' as described and illustrated herein.

* * * * *